US012667530B2

(12) United States Patent
Hippe et al.

(10) Patent No.: US 12,667,530 B2
(45) Date of Patent: Jun. 30, 2026

(54) AGENT FOR OXIDATIVELY DYEING KERATIN FIBERS

(71) Applicant: Henkel AG & Co. KGaA, Duesseldorf (DE)

(72) Inventors: Thomas Hippe, Appen (DE); Astrid Kleen, Haseldorf (DE); Hartmut Manneck, Barnitz (DE); Stefan Hoepfner, Hamburg (DE); Tugce Cansev, Hamburg (DE)

(73) Assignee: Henkel AG & Co. KGaA, Düsseldorf (DE)

(*) Notice: Subject to any disclaimer, the term of this patent is extended or adjusted under 35 U.S.C. 154(b) by 0 days.

(21) Appl. No.: 18/887,259

(22) Filed: Sep. 17, 2024

(65) Prior Publication Data

US 2025/0017837 A1 Jan. 16, 2025

Related U.S. Application Data

(63) Continuation of application No. PCT/EP2023/050057, filed on Jan. 3, 2023.

(30) Foreign Application Priority Data

Mar. 21, 2022 (DE) ......................... 102022202759.0

(51) Int. Cl.

| | |
|---|---|
| ***A61Q 5/10*** | (2006.01) |
| ***A61K 8/22*** | (2006.01) |
| ***A61K 8/41*** | (2006.01) |
| ***A61K 8/46*** | (2006.01) |
| ***A61K 8/49*** | (2006.01) |

(52) U.S. Cl.

CPC ................ *A61K 8/492* (2013.01); *A61K 8/22* (2013.01); *A61K 8/411* (2013.01); *A61K 8/415* (2013.01); *A61K 8/418* (2013.01); *A61K 8/46* (2013.01); *A61K 8/4926* (2013.01); *A61Q 5/10* (2013.01); *A61K 2800/882* (2013.01)

(58) Field of Classification Search

CPC .......... A61K 8/492; A61K 8/22; A61K 8/411; A61K 8/415; A61K 8/418; A61K 8/46; A61K 8/4926; A61K 2800/882; A61K 2800/30; A61K 2800/42; A61K 2800/4324; A61K 2800/88; A61K 8/34; A61K 8/466; A61Q 5/10

USPC .............................................................. 8/405

See application file for complete search history.

(56) References Cited

U.S. PATENT DOCUMENTS

| | | | | |
|---|---|---|---|---|
| 6,203,579 | B1 * | 3/2001 | Moeller | A61Q 5/10 8/405 |
| 2022/0151897 | A1 * | 5/2022 | Monda | A61K 8/86 |

FOREIGN PATENT DOCUMENTS

| | | | | | |
|---|---|---|---|---|---|
| DE | 2716671 | A1 | | 10/1978 | |
| DE | 102008056811 | A1 | | 9/2009 | |
| EP | 0977545 | B1 | * | 2/2005 | A61Q 5/10 |
| EP | 2559456 | B1 | | 9/2018 | |
| EP | 3943161 | A1 | | 1/2022 | |
| KR | 20060073522 | A | * | 6/2006 | A61Q 5/10 |
| WO | 9847472 | A1 | | 10/1998 | |
| WO | WO 0103660 | A1 | * | 1/2001 | A61Q 5/10 |
| WO | WO 2020188936 | A1 | * | 9/2020 | A61Q 5/10 |

OTHER PUBLICATIONS

"Description of a Proposed Reference Dose Resorcinol", Sep. 1, 2004 (Sep. 1, 2004), XP055300873, Gefunden im Internet: URL:http://www.dep.State.pa.us/dep/subject /advcoun/cleanup/2004/Dec8/AMEC_Resorcinol RFD_090804.pdf [gefunden am Sep. 8, 2016] Executive summary, ES-2 Hazard Identification, 3. Use of resorcinol, 5. Hazard identification, 5.1. Human.

PCT International Search Report—WO PCT/EP2023/050057—Completed: Apr. 4, 2023; Mailing date: Apr. 13, 2023—Number of pp. 149.

* cited by examiner

*Primary Examiner* — Eisa B Elhilo

(74) *Attorney, Agent, or Firm* — Blank Rome LLP

(57) ABSTRACT

An agent for oxidatively dyeing keratinous fibers, in particular human hair, containing, in a cosmetic carrier, at least one oxidation dye precursor or the developer type, isatin, and at least one oxidizing agent and related systems and methods.

17 Claims, No Drawings

AGENT FOR OXIDATIVELY DYEING KERATIN FIBERS

FIELD OF INVENTION

The present invention relates to a cosmetic means for oxidatively dyeing keratin fibers, containing at least one oxidation dye precursor of the p-phenylenediamine type (a), isatin (b), and at least one oxidizing agent (c). A further object is a multicomponent packaging unit (kit-of-parts) comprising the ingredients (a), (b) and (c) separately packaged in two containers. Another object is the use of (a) and (b) in order to generate color shades in the natural tone range on keratinous fibers, in particular human hair, in the presence of the oxidizing agent (c).

BACKGROUND

In order to provide color-changing cosmetic means, in particular for keratinous fibers, such as hair, a person skilled in the art is aware of various dyeing systems depending on the coloration requirement. For permanent, intense colorations having appropriate fastness properties, so-called oxidation dyes are used. Such dyes typically contain oxidation dye precursors, known as developer components, and coupler components, which together form the actual dyes under the influence of oxidizing agents, for example hydrogen peroxide. Oxidation dyes are characterized by outstanding, long-lasting coloring results.

The oxidation dye precursors (developers and couplers) themselves are not colored, but rather the actual dyes are formed only during the course of the application when the oxidation dye precursors come into contact with the oxidizing agent (hydrogen peroxide). In a chemical reaction, the developers used as oxidation dye precursors (such as p-phenylenediamine or derivatives thereof) are first oxidatively converted by hydrogen peroxide into a reactive intermediate, also called quinonimine or quinone diimine, which then reacts in an oxidative coupling reaction with the couplers to form the corresponding dye.

With oxidation dyes, hair can be dyed both in intensive mode shades and in natural shades by choosing the suitable developer components and coupler components. A large area of application for oxidation dyes is the coloring of gray hair in a natural shade, which resembles the hair color that the user had when they were younger. A person skilled in the art knows the use of developers based on the base body of 1,4-diaminobenzene (para-phenylenediamine) and couplers with a resorcinol structure (1,3-dihydroxybenzene) as a classic combination for producing oxidative colorations in the brown to dark-blond range.

Said oxidation dyes have been used for decades. Although they are only intended for extracorporeal use on keratin fibers such as head hair, eyelashes, and eyebrows, contact of the dye with the scalp cannot be completely avoided during use. In order to ensure the highest possible product safety for customers, the commercially available oxidation dye precursors are continuously checked for their physiological compatibility, for example by the Scientific Committee on Consumer Products (SCCP), an advisory body of the European Commission. It is known that some of the oxidation dye precursors, in particular some of the oxidation bases of the para-phenylenediamine type, can have a certain potential for sensitization. In order to rule out allergic reactions during or after the dyeing process, the customer is therefore recommended to perform a test with a small amount of the dye on the skin before using the dye on the hair. In addition to skin sensitization, other physiological effects are also monitored.

Resorcinol, 4-chlororesorcinol and 2-methylresorcinol are common oxidation dye precursors with a 1,3-dihydroxybenzene base body. In its last opinion from March 2021, SCCP came to the conclusion that the use of resorcinol in oxidative hair dyes with a resorcinol concentration of up to 1.25 wt. % in the ready-to-use mixture was considered safe. The SCCP stated that resorcinol has a thyroid-inhibiting effect. Although a definite level of exposure required for such an effect cannot be derived from the available studies in humans, most of these studies indicate a much higher exposure relatively than is the case in cosmetics.

In order to take into account the concerns of some consumers with regard to product safety, the object of the present invention was to provide a means for oxidatively dyeing keratin fibers, in particular human hair, with which a broad color spectrum can be covered, in particular a natural color pallet with cool natural shades and warm natural shades, and a gold color series which leads to colors having high fastness properties, without impairing product safety. In particular, dyeing in these natural shades should be possible without the use of couplers of the recyclin type.

Many users dye their hair over decades in the same shade and do not want a sudden, obvious, visible change to their usual hair color. For these users, it is therefore essential to allow the customary, resorcinol-containing hair dye to be replaced by a new, resorcinol-free product without a shift in shade. A central challenge of the present application was therefore to find a new, resorcinol-free hair dye which, in its color effect and its color result, corresponds as precisely as possible to the resorcinol-containing dye used to date.

DETAILED DESCRIPTION OF THE INVENTION

Surprisingly, it has now been found that this object can be achieved excellently by an oxidation dye which contains a developer with a p-phenylenediamine basic structure (a), isatin (b), and hydrogen peroxide or one of the addition products (c) thereof.

A first subject matter of the present invention is a means for oxidatively dyeing keratinous fibers, in particular human hair, containing, in a cosmetic carrier, a. at least one oxidation dye precursor of the developer type, selected from the group including p-toluenediamine, 2-methoxymethyl-p-phenylenediamine, 2-(2-hydroxyethyl)-p-phenylenediamine, N,N-bis(2-hydroxyethyl)-p-phenylenediamine, p-phenylenediamine and the physiologically acceptable salts thereof;
b. isatin and
c. at least one oxidizing agent from the group consisting of hydrogen peroxide and the addition products thereof with organic or inorganic compounds.

The research leading to this invention has shown that the oxidative dyeing of hair induced by hydrogen peroxide using a developer from the group of p-toluenediamine, 2-methoxymethyl-p-phenylenediamine, 2-(2-hydroxyethyl)-p-phenylenediamine, N,N-bis(2-hydroxyethyl)-p-phenylenediamine, p-phenylenediamine in combination with isatin leads to very intense colorations with excellent fastness properties. It was also particularly advantageous that the color effect of a corresponding resorcinol-containing dye could be accurately reproduced with this dye combination.

Keratin Fibers

Keratin fibers are, in principle, understood to mean all types of animal hair, for example wool, horsehair, angora hair, furs, feathers, and products or textiles manufactured therefrom. Preferably, however, the keratin fibers are human hair.

Means for Oxidation Dyeing

The term "means for oxidation dyeing" of keratin fibers used according to the invention is understood to mean oxidation dyes. Oxidative dyes contain oxidation dye precursors, so-called developers and coupler components. Developers and couplers diffuse separately into the keratin fibers and form the actual dyes in a chemical reaction with one another under the influence of an oxidizing agent (hydrogen peroxide). Depending on the quantity of oxidizing agent employed, the keratin fibers are simultaneously lightened to a greater or lesser extent during coloring, since the oxidizing agent not only initiates the dye-forming process of the developers and couplers, but also oxidatively destroys the hair's own pigments (melanins). Depending on the used amounts of the oxidation dye precursor products and of the oxidizing agent, the oxidative coloration can therefore be predominantly a coloration (with high dye proportion) or predominantly a lightening (with high proportion of oxidizing agent). In the latter case, the oxidation dye precursors are mostly used for shading the brightening result.

The means according to the invention contain the components essential to the invention in each case in a cosmetic carrier, preferably in a suitable aqueous, alcoholic, or aqueous-alcoholic carrier. For the purpose of hair coloring, such supports are for example creams, emulsions, gels or also surfactant-containing foaming solutions, such as for example shampoos, foam aerosols, form formulations or other preparations which are suitable for application to hair.

The oxidative dye described above is a ready-to-use dye which is applied in this form containing the components (a) and (b) and (c) for application onto the keratin fibers.

Oxidation Dye Precursors of Developer Type (a)

As a first substantial component, the oxidative dyes according to the invention contain at least one oxidation dye precursor of the developer type which is based on the base body of p-phenylenediamine. The oxidation dye precursor of the developer type or these oxidation dye precursors of the developer type are selected from the group consisting of p-toluylenediamine, 2-methoxymethyl-p-phenylenediamine, 2-(2-hydroxyethyl)-p -phenylenediamine, N,N-bis-(2-hydroxyethyl)-p-phenylenediamine, p-phenylenediamine, and the physiologically acceptable salts thereof. p-toluylenediamine is alternatively also referred to as 2,5-toluylenediamine, p-toluylenediamine (abbreviation: PTD), 2,5-diaminotoluene, 2-methyl-p-phenylenediamine or 2,5-diaminomethylbenzene. PTD has the CAS number 95-70-5. 2-methoxymethyl-p-phenylenediamine is alternatively also referred to as 2-methoxymethyl-1,4-benzenediamine and, in the form of its free base, bears the CAS number 337906-36-2. 2-(2-hydroxyethyl)-p-phenylenediamine is alternatively referred to as 2-(2,5-diaminophenyl) ethanol and, in the form of its free base, carries the CAS number 93841-24-8. N,N-bis-(2-hydroxyethyl)-p-phenylenediamine, in the form of its free base, has the CAS number 7575-35-1.

The developers of the above-mentioned group (a) can be used in the form of their free base or else in the form of their physiologically acceptable salts in the agent according to the invention. A physiologically acceptable salt is understood to mean a salt of the developer that is well tolerated by the user under physiological conditions, i.e., during use of the means. Physiologically acceptable salts are in particular the chlorides, bromides, sulfates, and hemisulfates of developers (a).

The means which contain at least one oxidation dye precursor of the developer type (a), which is selected from the group of p-toluylenediamine, 2-methoxymethyl-p -phenylenediamine and the physiologically acceptable salts thereof, have proven to be very particularly suitable for achieving the object according to the invention.

With an oxidative dye containing p-toluylenediamine and/or 2-methoxymethyl-p-phenylenediamine (or a salt thereof) as developer (a), hair was able to be dyed with very high intensity in natural shades. It was also particularly surprising that the hair could be colored in a shade which was particularly strongly similar to the shade obtained with a dye containing the classic combination of PDT and resorcinol.

In a particularly preferred embodiment, a means according to the invention is therefore characterized in that it contains at least one oxidation dye precursor of the developer type (a) which is selected from the group of p-toluylenediamine, 2-methoxymethyl-p-phenylenediamine and the physiologically acceptable salts thereof.

In a further particularly preferred embodiment, a means according to the invention is therefore characterized in that it contains at least one oxidation dye precursor of the developer type (a) which is selected from the group of p-toluylenediamine, p-toluylenediamine sulfate, p-toluylenediamine chloride, p-toluylenediamine bromide, 2-methoxymethyl-p-phenylenediamine, 2-methoxymethyl-p-phenylenediamine sulfate, 2-methoxymethyl-p-phenylenediamine chloride and 2-methoxymethyl-p-phenylenediamine bromide.

The developer or developers from the aforementioned group (a) are preferably used in specific quantity ranges in the means according to the invention. The means preferably contains, based on the total weight of the means, one or more oxidation dye precursors of developer type (a) in a total amount of from 0.001 to 10.0 wt. %, preferably from 0.01 to 6.0 wt. %, more preferably from 0.1 to 5.0 wt. %, and very particularly preferably from 0.15 to 4.7 wt. %.

In a particularly preferred embodiment, a means according to the invention is thus characterized in that the agent contains, based on the total weight of the agent, one or more oxidation dye precursors of developer type (a) in a total amount of 0.001 to 10.0 wt. %, preferably 0.01 to 6.0 wt. %, more preferably 0.1 to 5.0 wt. %, and very particularly preferably 0.15 to 4.7 wt. %.

In addition to the essential oxidation dye precursors of developer type (a), the means according to the invention can optionally also contain further developers. These further developers can be used in particular for fine tuning the desired color shade in the means. For example, the additional developers that are different to group (a) can be used in particular to develop shades in the natural red or natural copper range.

Depending on the desired color effect, it can therefore be preferred for the means to additionally contain one or more further oxidation dye precursors of the developer type, which are selected from the group of bis-(2-hydroxy-5-aminophenyl)methane, 1,3-bis-(2,5-diaminophenoxy) propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triamino-pyrimidine, 2,3-diamino-6,7-dihydro-1H, 5H-pyrazolo [1,2-a] pyrazol-1-one, and the physiologically acceptable salts thereof.

The developer or the additional developers can, based on the total weight of the means, be contained in the means in a total amount of from 0.001 to 10.0 wt. %, preferably from 0.01 to 6.0 wt. %, more preferably from 0.1 to 5.0 wt. %, and very particularly preferably from 0.15 to 4.7 wt. %.

Isatin

As a second component substantial to the invention, the oxidation dye is isatin (b). Isatin is the compound of formula (ISA), which can alternatively also be referred to as 2,3-indoline-dione or as 2,3-dioxoindoline (ISA)

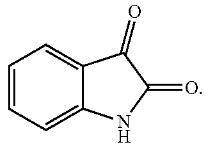

Isatin has the CAS number 91-56-5.

With regard to an optimal solution of the object according to the invention, isatin (b) is preferably contained in specific quantity ranges in the means according to the invention. Particularly good results were obtained when the means contained, based on the total weight of the means, 0.001 to 10 wt. %, preferably 0.01 to 5 wt. %, more preferably 0.1 to 3.5 wt. %, and very particularly preferably 0.15 to 2.5 wt. % isatin (b).

In a particularly preferred embodiment, a means according to the invention is thus characterized in that it contains, based on the total weight of the means, 0.001 to 10 wt. %, preferably 0.01 to 5 wt. %, more preferably 0.1 to 3.5 wt. %, and particularly preferably 0.15 to 2.5 wt. % isatin (b).

Isatin is commercially available from different suppliers, such as Acros, Sigma Aldrich, Thermo Scientific, etc.

Weight Ratio of Developers (a) to Isatin (b) on Average

The shade resulting from the coloration on the hair depends both on the amounts of developer(s) (a) used and on the amount of the isatins (b) contained in the means. As is known from typical dyeing practice, the higher the amounts of developers (a) and isatin (b) used, the higher the intensity of the coloration. However, the nature of the resulting coloring can be controlled by the quantitative ratio in which the developers of group (a) and isatin (b) are used in the oxidative dye.

The colors produced on the hair then had a particularly high similarity to the colorations obtained with the couplers of the resorcinol type if the means contained the developers (a) and isatin (b) in a weight ratio which has value of from 2:1 to 1:2, preferably from 1.9:1 to 1:1, more preferably from 1.9:1 to 1.1:1, even more preferably from 1.8:1 to 1.1:1, and very particularly preferably from 1.7:1 to 1.2:1. This effect was observed in particular in the darker natural shades, such as dark brown and medium blond.

In a particularly preferred embodiment, a means according to the invention is thus characterized in that the weight ratio of all the developers of the group (a) contained in the means to the isatin (b) contained in the means, i.e., the weight ratio (a)/(b), has a value of 2:1 to 1:2, preferably of 1.9:1 to 1:1, more preferably of 1.9:1 to 1.1:1, even more preferably of 1.8:1 to 1.1:1 and very particularly preferably of 1.7:1 to 1.2:1.

In the preferred weight ratio (a)/(b) of 1.9:1 to 1:1, for example, the developer (a) or developers (a) is/are used in the means either in the same amount as isatin (b) or in an up to 1.9-fold weight excess. Very particularly preferably, in comparison with the isatin (b), the developers (a) are used in a 1.2-fold to 1.7-fold weight excess.

Hydrogen Peroxide (c)

As a third substantial component, the oxidative dye according to the invention contains at least one oxidizing agent (c) from the group of hydrogen peroxide and its addition products with organic or inorganic compounds.

In a preferred embodiment, hydrogen peroxide itself is used as an aqueous solution in the oxidation dye. The concentration of a hydrogen peroxide solution is determined by the legal requirements, on one hand, and by the desired effect, on the other; preferably, 6 to 12 wt. % solutions in water are used. Oxidative that are preferred according to the invention are characterized in that they contain 0.5 to 20 wt %, preferably 1 to 12.5 wt. %, especially preferably 2.5 to 10 wt. %, and, in particular, 3 to 8 wt. % hydrogen peroxide, based in each case on the total weight of the oxidative dye.

In a particularly preferred embodiment, a means according to the present invention is thus characterized in that it contains, based on the total weight of the means, 0.5 to 20 wt. %, preferably 1 to 12.5 wt. %, more preferably 2.5 to 10 wt. %, and particularly preferably 3 to 8 wt. % hydrogen peroxide (c).

Further Couplers (d) in Oxidation Dyes

For precise shading and/or fine adjustment of the desired color shade, the oxidative dye can also contain further couplers (d) in addition to the oxidation dye precursors (a), optionally the further optionally usable developers and isatin (b).

Further very well suited couplers can be selected for example from the group consisting of 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethyl)-1-methylbenzene, 1-amino-3-bis (2-hydroxyethyl)aminobenzene, 2-amino-3-hydroxypyridine, 3-amino-2-methylamino -6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or mixtures of said compounds or the physiologically acceptable salts thereof.

In a particularly preferred embodiment, a means according to the invention is thus characterized in that it contains at least one oxidation dye precursor of the coupler type (d) which is selected from the group of 3-aminophenol, 5-amino-2-methylphenol, 3-amino -2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2(2,4-diaminophenoxy)ethanol, 1,3-bis(2,4-diaminophenoxy)propane, 1-methoxy-2-amino-4-(2-hydroxyethylamino benzene, 1,3-bis(2,4-diaminophenyl)propane, 2,6-bis(2'-hydroxyethyl)-1-methylbenzene, 1-amino-3-bis (2-hydroxyethyl)aminobenzene, 2-amino-3-hydroxypyridine, 3-amino-2-methylamino -6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or mixtures of said compounds or the physiologically acceptable salts thereof.

Particularly natural shades with great similarity to the corresponding resorcinol-containing dyes could be obtained if the dye additionally contained one or more couplers (d) which were selected from the group consisting of 3-aminophenol, 5-amino-2-methylphenol, 3-amino-2-chloro-6-methylphenol, 2-amino-3-hydroxypyridine, 1-methoxy-2-amino-4-(2-hydroxyethylamino)benzene, 6-hydroxyindole, or mixtures of these compounds or the physiologically acceptable salts thereof. For this reason, the use of couplers (d) from this group is explicitly very particularly preferred.

In an explicitly very particularly preferred embodiment, a means according to the invention is therefore characterized in that it contains at least one oxidation dye precursor of coupler type (d) which is selected from the group consisting of 3-aminophenol, 5-amino-2-methylphenol, 3-amino-2-chloro-6-methylphenol, 2-amino-3-hydroxypyridine, 1-methoxy-2-amino-4-(2-hydroxyethyl amino)benzene, 6-hydroxyindole, or mixtures of said compounds or the physiologically acceptable salts thereof.

The couplers from the above-described group (d) are also preferably used in specific quantity ranges in the means according to the invention. Particularly positive results were obtained when the means contained, based on the total weight of the agent, one or more oxidation dye precursors of the coupler type (d) in a total amount of 0.001 to 10 wt. %, preferably 0.01 to 5 wt. %, more preferably 0.1 to 3.5 wt. %, and very particularly preferably 0.15 to 2.5 wt. %.

In a further preferred embodiment, a means according to the invention is characterized in that the means contains, based on the total weight of the means, one or more oxidation dye precursors of the coupler type (d) in a total amount of 0.001 to 10 wt. %, preferably 0.01 to 5 wt. %, more preferably 0.1 to 3.5 wt. %, and very particularly preferably 0.15 to 2.5 wt. %.

Dispensing With Resorcinol-Type Couplers

As already described above, with the means of the present application, intense colorations in the natural tone range should be developed, which reproduce the shades that are produced with resorcinol-containing dyes as well as possible, without being dependent on the use of couplers of the resorcinol type.

Resorcinol-type couplers or couplers from the group of resorcinols are understood to mean 1,3-dihydroxybenzene and derivatives thereof. Derivatives of 1,3-dihydroxybenzene are all compounds which have a 1,3-dihydroxybenzene basic structure and can carry further substituents, wherein both hydroxyl groups of the 1,3-dihydroxbenzene must still be present.

The couplers from the group of resorcinols used as standard in market products are resorcinol, 2-methylresorcinol, and 4-chlororesorcinol. Couplers from the group of resorcinols are therefore understood in particular to be resorcinol, 2-methylresorcinol, and 4-chlororesorcinol. In the means of the present application, these couplers are to be dispensed with, and therefore it is preferred if the total amount of precursors of the coupler type contained in the means from the group of resorcinols, in particular from the group consisting of resorcinol, 2-methylresorcinol, and 4-chlororesorcinol, is below 0.1 wt. %, preferably below 0.05 wt. %, particularly preferably below 0.01 wt. %, and very particularly preferably 0 wt. %.

In a further very particularly preferred embodiment, a means according to the invention is therefore characterized in that, based on the total weight of the agent, the total amount of the oxidation dye precursors of the coupler type contained in the means is from the group of resorcinols, in particular from the group consisting of resorcinol, 2-methylresorcinol, and 4-chlororesorcinol, is below 0.1 wt. %, preferably below 0.05 wt. %, particularly preferably below 0.01 wt. %, and very particularly preferably 0 wt. %.

Substantive Dyes

Furthermore, the means according to the invention can optionally contain at least one substantive dye. These are dyes which are drawn directly onto the hair and which do not require an oxidative process in order to form the color. Direct dyes are usually nitrophenylenediamines, nitroaminophenols, azo dyes, anthraquinones, triarylmethane dyes, or indophenols.

The substantive dyes are each used preferably in an amount of from 0.001 to 20 wt. %, in particular from 0.05 to 5 wt. %, in each case in relation to the total preparation for use. The total quantity of substantive dyes is preferably at most 3 wt. %.

Substantive dyes can be divided into anionic, cationic and non-ionic substantive dyes, which are selected and used by a person skilled in the art according to the requirements of the support base.

Preferred anionic direct dyes are the compounds known under the international names or trade names Bromophenol Blue, Tetrabromophenol Blue, Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, and Acid Black 52.

Preferred cationic direct dyes are Basic Blue 7, Basic Blue 26, Basic Violet 2 und Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Yellow 87, Basic Orange 31, and Basic Red 51.

In particular, non-ionic nitro dyes and quinone dyes and neutral azo dyes are suitable as non-ionic direct dyes. Preferred non-ionic direct dyes are the compounds known under the international names or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and also 1,4-diamino-2-nitrobenzene, 2-amino-4-nitrophenol, 1,4-bis(2-hydroxyethyl)amino -2-nitrobenzene, 3-nitro-4-(2-hydroxy-ethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino] benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol.

Alkalizing Agent

Coloring processes on keratin fibers typically take place in an alkaline environment. To protect the keratin fibers as well as the skin as much as possible, however, it is not desirable to adjust to too high a pH value. It is therefore preferred if the pH of the ready-to-use means is between 6 and 11, in particular between 7 and 10.5. The pH values within the meaning of the present invention are pH values which have been measured at a temperature of 22° C.

The alkalizing agents that can be used to adjust the preferred pH according to the invention can be selected from the group formed by ammonia, alkanolamines, basic amino acids, and inorganic alkalinizing agents, such as alkali (alkaline earth) metal hydroxides, alkali (alkaline earth) metal metasilicates, alkali (alkaline earth) metal phosphates, and alkali (alkaline earth) metal hydrogen phosphates. Preferred inorganic alkalinizing agents are magnesium carbonate, sodium hydroxide, potassium hydroxide, sodium silicate, and sodium metasilicate. Organic alkalizing agents that can be used according to the present invention are preferably selected from monoethanolamine, 2-amino-2-methylpropanol, and triethanolamine. The basic amino acids that can be used as an alkalizing agent according to the present invention are preferably selected from the group consisting of arginine, lysine, ornithine, and histidine, especially preferably arginine.

Additional Ingredients in the Means

Preferably, an emulsifier or a surfactant is also added to the oxidative dyes, wherein surface-active substances are referred to as surfactants or emulsifiers depending on the field of application and are selected from anionic, cationic, zwitterionic, amphoteric and nonionic surfactants and emulsifiers.

In a further very particularly preferred embodiment, a means according to the invention is therefore characterized in that it contains at least one surfactant selected from the group consisting of anionic, amphoteric, zwitterionic, and non-ionic surfactants.

Suitable anionic surfactants in the means according to the invention are all anionic surface-active substances suitable for use on the human body. These are characterized by a water-solubilizing, anionic group, such as for example a carboxylate, sulfate, sulfonate or phosphate group, and a lipophilic alkyl group having about 8 to 30 carbon atoms. In addition, glycol ether or polyglycol ether groups, ester, ether and amide groups, and hydroxyl groups can be contained in the molecule. Examples of suitable anionic surfactants are, in each case in the form of the sodium, potassium and ammonium and mono-, di- and trialkanolammonium salts having 2 to 4 C atoms in the alkanol group, linear and branched fatty acids having 8 to 30 C atoms (soaps);

ether carboxylic acids of the formula $RO(CH_2CH_2O)_x CH_2COOH$, in which R is a linear alkyl group having 8 to 30 C atoms and x=0 or 1 to 16, acyl sarcosides having 8 to 24 C atoms in the acyl group;

acyl taurides having 8 to 24 C atoms in the acyl group;

acyl isethionates having 8 to 24 C atoms in the acyl group;

sulfosuccinic acid mono- and dialkyl esters having 8 to 24 C atoms in the alkyl group and sulfosuccinic acid monoalkyl polyoxyethyl esters having 8 to 24 C atoms in the alkyl group and 1 to 6 oxyethyl groups;

linear alkane sulfonates having 8 to 24 C atoms;

linear a-olefin sulfonates having 8 to 24 C atoms;

sulfonates of unsaturated fatty acids having 8 to 24 C atoms and 1 to 6 double bonds, asulfo fatty acid methyl esters of fatty acids having 8 to 30 C atoms;

alkyl sulfates and alkyl ether sulfates of the formula $RO(CH_2CH_2O)_xSO_3H$, in which R is a preferably linear alkyl group having 8 to 30 C atoms and x=0 or 1 to 12;

mixtures of surface-active hydroxy sulfonates, sulfated hydroxyalkyl polyethylene and/or hydroxyalkylene propylene glycol ethers, esters of tartaric acid and citric acid with alcohols, which represent addition products of about 2-15 molecules ethylene oxide and/or propylene oxide to fatty alcohols having 8 to 22 C atoms, alkyl and/or alkenyl ether phosphates of the formula

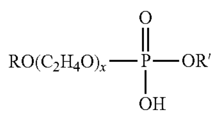

in which R preferably represents an aliphatic, optionally unsaturated hydrocarbon radical having 8 to 30 carbon atoms, R' represents hydrogen, a radical $(CH_2CH_2O)_yR$ and x and y independently of one another represent a number from 1 to 10, sulfated fatty acid alkylene glycol esters of the formula $RC(O)O(alkO)_nSO_3$, in which R represents a linear or branched, aliphatic, saturated and/or unsaturated alkyl functional group having 6 to 22 C atoms, alk represents $CH_2CH_2$, $CHCH_3CH_2$ and/or $CH_2CH$ $CH_3$ and n represents a number from 0.5 to 5, monoglyceride sulfates and monoglyceride ether sulfates.

Preferred anionic surfactants are alkyl sulfates, alkyl ether sulfates and ethercarboxylic acids having 10 to 18 carbon atoms in the alkyl group and up to 12 glycol ether groups in the molecule.

Surface-active compounds that carry, in the molecule, at least one quaternary ammonium group and at least one carboxylate, sulfonate or sulfate groups are referred to as zwitterionic surfactants. Particularly suitable zwitterionic surfactants are the so-called betaines, such as the N-alkyl-N,N-dimethylammonium glycinates, for example cocoalkyl dimethylammonium glycinate; the N-acylaminopropyl-N,N-dimethylammonium glycinates, for example cocoacylaminopropyl dimethylammonium glycinate; and 2-alkyl -3-carboxymethyl-3-hydroxyethyl imidazolines each having 8 to 18 C atoms in the alkyl or acyl group, and cocoacylaminoethyl hydroxyethyl carboxymethyl glycinate. A preferred zwitterionic surfactant is the fatty acid amide derivative known under the INCI name Cocamidopropyl Betaine.

Amphoteric surfactants are understood to be surface-active compounds which, in addition to a $C_8$-$C_{24}$ alkyl or acyl group, also contain at least one free amino group and at least one —COOH— or —$SO_3H$ group in the molecule and are capable of forming inner salts. Examples of suitable amphoteric surfactants are N-alkylglycines, N-alkylpropionic acids, N-alkylaminobutyric acids, N-alkyliminodipropionic acids, N-hydroxyethyl-N -alkylamidopropylglycines, N-alkyltaurines, N-alkylsarcosines, 2-alkylaminopropionic acids and alkylaminoacetic acids having in each case about 8 to 24 carbon atoms in the alkyl group. Particularly preferred amphoteric surfactants are N-coco-alkylaminopropionate, coco-acylaminoethylaminopropionate, and $C_{12}$-$C_{18}$-acyl sarcosine.

It has also proven to be advantageous if the coloring and lightening agents according to the invention contain further, nonionogenic surface-active substances. Non-ionic surfactants contain, as hydrophilic group, for example a polyol group, a polyalkylene glycol ether group or a combination of polyol group and polyglycol ether group. Such compounds include, for example

- addition products of 1 to 50 mol of ethylene oxide and/or 0 to 5 mol of propylene oxide onto linear and branched fatty alcohols having 8 to 30 carbon atoms, such as for example lauryl, myristyl, cetyl, but also stearyl, isostearyl and oleyl alcohol, onto fatty acids having 8 to 30 carbon atoms and onto alkylphenols having 8 to 15 carbon atoms in the alkyl group,
- addition products end-capped with a methyl- or $C_2$-$C_6$ alkyl functional group of 1 to 50 mol ethylene oxide alkyl and/or 0 to 5 mol propylene oxide to linear and branched fatty alcohols with 8 to 30 carbon atoms, to fatty acids with 8 to 30 carbon atoms, and to alkylphenols with 8 to 15 carbon atoms in the alkyl group, such as those available type under the trade names Dehydol® LS, Dehydol® LT (Cognis),
- polyglycerol esters and alkoxylated polyglycerol esters, such as for example poly(3) glycerol diisostearate (commercial product: ®LameformTGI (Henkel)) and poly(2) glycerol polyhydroxystearate (commercial product: Dehymuls®PGPH (Henkel)).
- polyol fatty acid esters, such as the commercial product Hydagen® HSP (Cognis) or Sovermol-types (Cognis),
- more highly alkoxylated, preferably propoxylated and in particular ethoxylated mono-, di- and triglycerides, such as glycerol monolaurate+20 ethylene oxide and glycerol monostearate+20 ethylene oxide,
- amine oxides,
- hydroxy mixed ethers,
- sorbitan fatty acid esters and addition products of ethylene oxide to sorbitan fatty acid esters, such as e.g. polysorbates and sorbitol monolaurate+20 mol ethylene oxide (EO),
- sugar fatty acid esters and addition products of ethylene oxide to sugar fatty acid esters,
- addition products of ethylene oxide to fatty acid alkanolamides and fatty amines,
- fatty acid-N-alkyl glucamides,
- alkylphenols and alkylphenol alkoxylates having 6 to 21, in particular 6 to 15, carbon atoms in the alkyl chain and 1 to 30 ethylene oxide and/or propylene oxide units. Preferred representatives of this class include nonylphenol+9 EO and octylphenol+8 EO;
- alkyl polyglycosides corresponding to the general formula RO—$(Z)_x$, wherein R denotes an alkyl, Z denotes a sugar, and x denotes the number of sugar units. Alkyl polyglycosides usable according to the present invention may contain only one specific alkyl residue R. However, these compounds are normally prepared from natural fats and oils or mineral oils. In this case, the alkyl groups R are present as mixtures corresponding to the starting compounds or to the particular working-up of those compounds.

Particularly suitable nonionic surfactants are $C_8C_{22}$-alkyl monoglycosides and -alkyl oligoglycosides and their ethoxylated analogs. In particular, non-ethoxylated compounds have proven to be particularly suitable.

Particularly preferred are those alkyl polyglycosides of the formula RO—$(Z)_x$ where R

- substantially consists of $C_8$ and $C_{10}$ alkyl groups,
- substantially consists of $C_{12}$ and $C_{14}$ alkyl groups,
- substantially consists of $C_8$ to $C_{16}$ alkyl groups or
- substantially consists of $C_{12}$-to $C_{16}$ alky groups or
- substantially consists of $C_{16}$ to $C_{18}$ alkyl groups.

These compounds are characterized in that any mono- or oligosaccharides can be used as sugar building block Z. Usually, sugars with 5 or 6 carbon atoms as well as the corresponding oligosaccharides are used. Such sugars are, for example, glucose, fructose, galactose, arabinose, ribose, xylose, lyxose, allose, altrose, mannose, gulose, idose, talose, and sucrose. Preferred sugar building blocks are glucose, fructose, galactose, arabinose and sucrose; glucose is particularly preferred.

The alkylpolyglycosides which can be used according to the invention contain on average 1.1 to 5 sugar units. Alkylpolyglycosides having x values of 1.1 to 2.0 are preferred. Very particular preference is given to alkylglycosides in which x is 1.1 to 1.8.

The alkoxylated homologs of said alkylpolyglycosides can also be used according to the invention. These homologs may contain on average up to 10 ethylene oxide and/or propylene oxide units per alkylglycoside unit.

Addition products of alkylene oxide to saturated linear fatty alcohols and fatty acids containing from 2 to 30 mol ethylene oxide per mol of fatty alcohol or acid, have proved to be suitable as further preferred non-ionic surfactants. Preparations with excellent properties are likewise obtained if they contain fatty acid esters of ethoxylated glycerol as the nonionic surfactants.

Particularly preferred non-ionogenic surface-active substances are, because of the simple processability, substances which are commercially available in pure form as solids or liquids. In this context, the definition for purity does not refer to chemically pure compounds. Rather, in particular if the products have a natural base, mixtures of different homologues can be used, for example with different alkyl chain lengths, as obtained in products based on natural fats and oils. Mixtures of different degrees of alkoxylation are usually also present in alkoxylated products. In this context, the term purity refers instead to the fact that the selected substances should preferably be free of solvents, controls and other accompanying substances.

Products with a "normal" homolog distribution as well as those with a narrow homolog distribution may be used as surfactants which are addition products of ethylene and/or propylene oxide to fatty alcohols or derivatives of these addition products. "Normal" homolog distribution is to be understood in this case as mixtures of homologs which are obtained when reacting fatty alcohol and alkylene oxide using alkali metals, alkali metal hydroxides or alkali metal alkoxides as catalysts. In contrast, a narrow homolog distribution is obtained when hydrotalcites, alkaline-earth metal salts of ether carboxylic acids, alkaline-earth metal oxides, hydroxides or alkoxides for example are used as catalysts. The use of products with a narrow homolog distribution range may be preferred.

The anionic, nonionic, zwitterionic or amphoteric surfactants are used in amounts of 0.1 to 45 wt. %, preferably 1 to 30 wt. % and very particularly preferably 1 to 15% wt. %, based on the total amount of the ready-to-use agent.

Also preferred according to the invention are cationic surfactants of the quaternary ammonium compound, esterquat and amidoamine type. Preferred quaternary ammonium compounds are ammonium halides, in particular chlorides and bromides, such as alkyl trimethyl ammonium chlorides, dialkyl dimethyl ammonium chlorides, and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride, and tricetyl methyl ammonium chloride, and the imidazolium compounds known under the INCI names Quaternium-27 and Quaternium-83. The long alkyl chains of the aforementioned surfactants preferably have 10 to 18 carbon atoms. The quaternized protein hydrolysates represent other cationic surfactants that can be used according to the invention.

The alkylamidoamines are usually prepared by amidation of natural or synthetic fatty acids and fatty acid fractions with dialkylaminoamines and are characterized by their good biodegradability alongside a good conditioning effect. One compound from this substance group which is particularly suitable according to the invention is the stearamidopropyl dimethylamine available commercially under the name Tegoamid® S 18.

Also highly biodegradable are quaternary ester compounds, so-called "esterquats." Esterquats are known substances that contain both at least one ester function and at least one quaternary ammonium group as structural element. Preferred esterquats are quaternized ester salts of fatty acids with triethanolamine, quaternized ester salts of fatty acids with diethanolalkylamines and quaternized ester salts of fatty acids with 1,2-dihydroxypropyldialkylamines. Such products are sold for example under the trademarks Stepantex®, Dehyquart® and Armocare®. The products Armocare® VGH-70, an N,N-bis(2-palmitoyloxyethyl)dimethylammonium chloride, and Dehyquart® F-75, Dehyquart® C-4046, Dehyquart® L80 and Dehyquart® AU-35 are examples of such esterquats.

The cationic surfactants are contained in the agents used according to the invention preferably in amounts of 0.05 to 10% by weight, based on the total agent. Particular preference is given to amounts of 0.1 to 5% by weight.

In one preferred embodiment, preference may be given to nonionic, zwitterionic and/or amphoteric surfactants and mixtures thereof.

In a further preferred embodiment, the effect of the active ingredient according to the invention can be enhanced by emulsifiers. Such emulsifiers are for example

- addition products of 4 to 30 mol of ethylene oxide and/or 0 to 5 mol of propylene oxide to linear fatty alcohols having 8 to 22 C atoms, to fatty acids having 12 to 22 C atoms, and to alkylphenols having 8 to 15 C atoms in the alkyl group,
- $C_{12}$-$C_{22}$ fatty acid monoesters and diesters of addition products of 1 to 30 mol of ethylene oxide onto polyols having 3 to 6 carbon atoms, in particular onto glycerol, ethylene oxide and polyglycerol addition products to methyl glucoside fatty acid esters, fatty acid alkanolamides, and fatty acid glucamides,
- $C_8$-$C_{22}$ alkyl mono- and oligoglycosides and the ethoxylated analogs thereof, preference being given to degrees of oligomerization of 1.1 to 5, in particular 1.2 to 2.0, and glucose as the sugar component,
- mixtures of alkyl (oligo)glucosides and fatty alcohols, for example, the commercially available product Montanov® 68,
- addition products of 5 to 60 mol ethylene oxide to castor oil and hydrogenated castor oil,
- partial esters of polyols having 3 to 6 carbon atoms with saturated fatty acids having 8 to 22 carbon atoms,
- sterols, sterols being understood to mean a group of steroids which carry a hydroxyl group on carbon atom 3 of the steroid backbone and are isolated both from animal tissue (zoo sterols) and plant fats (phytosterols). Examples of zoosterols include cholesterol and lanosterol. Examples of suitable phytosterols include ergosterol, stigmasterol, and sitosterol. There are also sterols that are isolated from fungi and yeasts (so-called mycosterols).
- phospholipids, especially glucose phospholipids, which are obtained for example as lecithins or phosphatidylcholines from for example egg yolk or plant seeds (for example soya beans),
- fatty acid esters of sugars and sugar alcohols, such as sorbitol,
- polyglycerols and polyglycerol derivatives, such as for example polyglycerol poly-12-hydroxystearate (commercial product: Dehymuls® PGPH)
- linear and branched fatty acids having 8 to 30 carbon atoms, and the Na, K, ammonium, Ca, Mg and Zn salts thereof.

The means according to the invention contain the surfactants preferably in amounts of 0.1 to 25 wt. % in particular 0.5 to 15 wt. % based on the total amount of the ready-to-use agent.

According to the invention, particular preference may be given to nonionogenic emulsifiers and surfactants having an HLB value of 10-15. Among these emulsifier types, very particular preference may be given to those emulsifiers which contain no ethylene oxide and/or propylene oxide in the molecule.

Further work has shown that the oxidative formation of intense colorations from the components (a) and (b) functions in particular in the cosmetic carrier formulations which do not have an excessively high fat component content. A strong color application was then observed in particular if, based on the total weight of the agent, the total amount of the fat components contained in the agent was below 25 wt. %, preferably below 20 wt. %, more preferably below 15 wt. %, and very particularly preferably below 13 wt. %.

In the context of a further preferred embodiment, an agent according to the invention is characterized in that, based on the total weight of the agent, the total content of the fatty components contained in the agent is below 25 wt. %, preferably below 20 wt. %, further preferably below 15 wt. %, and very particularly preferably below 13 wt. %.

Fatty components within the context of the invention are understood to be organic compounds with a solubility in water of less than 1 wt. %, and preferably less than 0.1 wt. % at room temperature (22° C.) and atmospheric pressure (760 mmHg).

Under the definition of fat components fall explicitly only uncharged (i.e., non-ionic) compounds. Fat constituents have at least one saturated or unsaturated alkyl group having at least 8 C atoms. The molecular weight of the fat component is at most 5,000 g/mol, preferably at most 2,500 g/mol, and particularly preferably at most 1,000 g/mol. The fat components are either polyoxyalkylated or polyglycerylated compounds.

In this context, fatty components are understood to be components from the group of $C_{12}$-$C_{30}$ fatty alcohols, $C_{12}C_{30}$ fatty acid triglycerides and/or hydrocarbons. Within the meaning of the present invention, explicitly only non-ionic substances are considered as fatty components. Charged compounds, such as fatty acids and salts thereof, are not understood to be fatty components.

$C_{12}$-$C_{30}$ fatty alcohols can be saturated, mono- or poly-unsaturated, linear or branched fatty alcohols having 12 to 30 C atoms.

Examples of preferred linear saturated $C_{12}$-$C_{30}$ fatty alcohols are dodecan-1-ol (dodecyl alcohol, lauryl alcohol), tetradecan-1-ol (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), arachyl alcohol (eicosan-1-ol), heneicosyl alcohol (heneicosan-1-ol) and/or behenyl alcohol (docosan-1-ol).

Linear unsaturated fatty alcohols are, for example, (9Z)-octadec-9-en-1-ol (oleyl alcohol), (9E)-octadec-9-en-1-ol (elaidyl alcohol), (9,12Z)-octadeca-9,12-dien-1-ol (linoleyl alcohol), (9Z,12Z,15Z)-octadeca-9,12,15-trien-1-ol (linolenoyl alcohol), gadoleyl alcohol ((9Z)-eicos-9-en-1-ol), arachidone alcohol ((5Z,8Z,11Z,14Z)-eicosa-5,8,11,14-tetraen-1-ol), erucyl alcohol ((13Z)-docos-13-en-1-ol), and/or brassidyl alcohol ((13E) -docosen-1-ol).

For a $C_{12}$-$C_{30}$ fatty acid triglyceride, in the context of the present invention, the triesters of trivalent alcohol glycerol are understood with three equivalents of fatty acid. Both structurally similar and different fatty acids may be involved in the ester formation within a triglyceride molecule.

According to the invention, fatty acids are to be understood as saturated or unsaturated, unbranched or branched, unsubstituted or substituted $C_{12}$-$C_{30}$ carboxylic acids. Unsaturated fatty acids may be mono-unsaturated or poly-unsaturated. With an unsaturated fatty acid, the C—C double bond(s) thereof may have the cis or trans configuration.

By way of example, esters originating from glycerol having a fatty acid can be named as fatty acid triglycerides, wherein the fatty acid is selected from the group consisting of dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z) -docos-13-enoic acid], linoleic acid [(9Z,12Z)-octadeca-9,12-dienoic acid], linolenic acid [(9Z,12Z,15Z)-octadeca-9,12,15-trienoic acid], eleostearic acid [(9Z,11E, 13E)-octadeca -9,11,3-trienoic acid], arachidonic acid [(5Z, 8Z,11Z,14Z)-eicosa-5,8,11,14-tetraenoic acid], and/or nervonic acid [(15Z)-tetracos-15-enoic acid].

The fatty acid triglycerides may also be of natural origin. The fatty acid triglycerides or mixtures thereof, for example corresponding natural fatty acid triglycerides, occurring in soybean oil, groundnut oil, olive oil, sunflower oil, macadamia nut oil, moringa oil, apricot kernel oil, marula oil and/or optionally hydrogenated castor oil.

Hydrocarbons are compounds having 8 to 80 C atoms composed exclusively of carbon and hydrogen atoms. Especially preferred in this context are aliphatic hydrocarbons, such as mineral oils, liquid paraffin oils (e.g., paraffinum liquidum or paraffinum perliquidum), isoparaffin oils, semi-solid paraffin oils, paraffin waxes, solid paraffin (paraffinum solidum), Vaseline, and polydecene.

In this respect, liquid paraffin oils (Paraffinum Liquidum and Paraffinum Perliquidum) have proven to be particularly suitable. The hydrocarbon is very particularly preferably Paraffinum Liquidum, also referred to as white oil. Paraffinum Liquidum is a mixture of purified, saturated, aliphatic hydrocarbons, consisting mainly of hydrocarbon chains having a C-chain distribution of from 25 to 35 C atoms.

Furthermore, it has proved advantageous if the according to the invention contain at least one stabilizer or complexer. Conventional complexing agents and stabilizers that are preferred within the scope of the present invention are, for example, polyoxycarboxylic acids, polyamines, ethylenediaminetetraacetic acid (EDTA), N-hydroxyethylethylenediaminetriacetic acid, diethylenetriaminepentaacetic acid (DTPA), ethylenediaminedisuccinic acid (EDDS), hydroxyethyliminodiacetic acid, nitridodiacetic acid-3-propionic acid, isoserindiacetic acid, N,N-di-(2-hydroxyethyl)glycine, N-(1,2-dicarboxy-2-hydroxyethyl)glycine, N-(1,2-dicarboxy-2-hydroxyethyl)aspartic acid or nitrilotriacetic acid (NTA), ethylenediaminediglutaric acid (EDGA), 2-hydroxypropylenediaminedisuccinic acid (HPDS), glycinamide-N, N'-disuccinic acid (GADS), cthylenediamine-N-N'-diglutaric acid (EDDG), 2-hydroxypropylenediamine-N -N'-disuccinic acid (HPDDS), diaminoalkyldi-(sulfosuccinic acid) (DDS), ethylenedicysteic acid (EDC), ethylenediamine-N-N'-bis-(ortho-hydroxyphenyl)acetic acid (EDDHA), N-2-hydroxyethylamine-N,N-diacetic acid, glyceryliminodiacetic acid, iminodiacetic acid-N-2-hydroxypropylsulfonic acid, aspartic acid-N-carboxymethyl-N -2,5-hydroxypropyl-3-sulfonic acid, B-alanine-N,N'-diacetic acid, aspartic acid-N,N'-diacetic acid, aspartic acid-N-monoacetic acid, dipicolinic acid, and salts and/or derivatives thereof, geminal diphosphonic acids such as 1-hydroxyethane-1,1-diphosphonic acid (HEDP), the higher homologs thereof with up to 8 carbon atoms, and also derivatives hereof containing hydroxy or amino groups and 1-aminoethane-1,1-diphosphonic acid, the higher homologs thereof with up to 8 carbon atoms, and also derivatives containing hydroxy or amino groups, aminophosphonic acids such as ethylenediamine tetra(methylene phosphonic acid) (EDTMP), diethylenetriamine penta(methylene phosphonic acid) (DTPMP) and higher homologs thereof, or nitrilotris(methylene phosphonic acid), phosphonopolycarboxylic acids such as 2-phosphonobutane-1,2,4-tricarboxylic acid, cyclodextrins, and alkali stannates (sodium stannate), alkalipyrophosphates (tetrasodiumpyrophosphate, disodiumpyrophosphate), alkaliphosphates (sodium phosphate), and phosphoric acid and salts thereof.

In the alkali pH values required according to the invention of the treatment solutions, these complexers are present at least partially as anions. It does not matter whether they are introduced in the form of acids or in the form of salts. If used as salts, preference is given to alkali, ammonium or alkylammonium salts, in particular sodium salts.

Complexers preferred according to the invention are nitrogen-containing polycarboxylic acids, in particular EDTA, and phosphonates, preferably hydroxyalkane or aminoalkane phosphonates and in particular 1-hydroxyethane-1,1-diphosphonate (HEDP) or the di- or tetra sodium salt thereof, and/or ethylenediaminetetramethylenephosphonate (EDTMP) or the hexasodium salt thereof, and/or diethylenetriaminepentamethylenephosphonate (DTPMP) or the hepta- or octasodium salt thereof.

The dyes according to the invention can preferably contain further auxiliary substances and additives. For instance, it has proven to be preferred according to the invention if the means contain at least one thickening agent. There are no basic restrictions with regard to these thickeners. Both organic and purely inorganic thickeners may be used.

According to a first preferred embodiment, the thickening agent is an anionic, synthetic polymer. Preferred anionic groups are the carboxylate group and the sulfonate group.

The examples of anionic monomers, which the polymeric anionic thickening agents may consist of, are acrylic acid, methacrylic acid, crotonic acid, itaconic acid, maleic anhydride and 2-acrylamido-2-methylpropanesulfonic acid. Here, the acidic groups may be present wholly or partly as sodium-, potassium-, ammonium-, mono- or triethanolammonium salt. Preferred monomers are maleic acid anhydride, and in particular, 2-acrylamido-2-methylpropane sulfonic acid and acrylic acid.

Preferred anionic homopolymers are uncrosslinked and crosslinked polyacrylic acids. Here, allyl ethers of pentaerythritol, sucrose and propylene may be preferred crosslinking agents. Such compounds are commercially available, for example, under the trade name Carbopol®. Also preferred is the homopolymer of 2-acrylamido-2-methyl propane sulfonic acid, which is commercially available, for example, under the name Rheothik®11-80.

Within this first embodiment, it may further be preferred to use copolymers of at least one anionic monomer and at least one nonionic monomer. With regard to the anionic monomers, reference is made to the substances listed above. Preferred non-ionic monomers are acrylamide, methacrylamide, acrylic acid esters, methacrylic acid esters, itaconic acid monoesters and diesters, vinyl pyrrolidinone, vinyl ethers, and vinyl esters.

The anionic acrylic acid and/or methacrylic acid polymers or copolymers are contained in the means according to the invention preferably in an amount of 0.1 to 10 wt. %, particularly preferably 1 to 5% wt %, in each case based on the weight of the means.

Preferred anionic copolymers are, for example, copolymers of acrylic acid, methacrylic acid or their $C_1$-$C_6$-alkyl esters, such as are marketed under the INCI name acrylate copolymers. One preferred commercial product is Aculyn® 33 from Rohm & Haas, for example. However, copolymers of acrylic acid, methacrylic acid or their $C_1$-$C_6$ alkyl esters and the esters of an ethylenically unsaturated acid and an alkoxylated fatty alcohol are further preferred. Suitable ethylenically unsaturated acids are in particular acrylic acid, methacrylic acid and itaconic acid, and suitable alkoxylated fatty alcohols are in particular Steareth-20 or Ceteth-20. Such copolymers are marketed by Rohm & Haas under the trade name Aculyn®22 and by National Starch under the trade names Structure®2001 and Structure®3001.

Further preferred anionic copolymers are acrylic acid-acrylamide-copolymers as well as in particular polyacrylamide copolymers with monomers containing sulfonic acid group. A particularly preferred anionic copolymer consists of 70 to 55 mol % of acrylamide and 30 to 45 mol % of 2-acrylamido-2-methylpropane sulfonic acid, wherein the sulfonic acid group is wholly or partially present as sodium-, potassium-, ammonium-, mono- or triethanolammonium salt. This copolymer can also be crosslinked, wherein preferably polyolefinically unsaturated compounds, such as tetraallyloxythane, allylsucrose, allylpentaerythritol and methylene-bisacrylamide, are used as crosslinking agents. Such a polymer is contained in the commercial products Sepigel®305 and Simulgel® 600 from the company SEPPIC. The use of these compounds, which contain a hydrocarbon mixture ($C_{13}$-$C_{14}$ isoparaffin or isohexadecane) and a non-ionic emulsifier (Laureth-7 or Polysorbate-80) in addition to the polymer components, has proved to be particularly advantageous in the context of the teaching of the invention.

Also, polymers of maleic acid anhydride and methyl vinyl ether, in particular those with crosslinks, are preferredthickening agents. The maleic acid methyl-vinyl ether -copolymer crosslinked with 1,9-decadiene is available under the name Stabileze®QM.

According to another embodiment, the thickener is a cationic synthetic polymer. Preferred cationic groups are quaternary ammonium groups. In particular, those polymers, in which the quaternary ammonium group is bonded to a polymer backbone built-up of acrylic acid, methacrylic acid or derivatives thereof via a $C_1$-$C_4$ hydrocarbon group, have been found to be particularly suitable.

Homopolymers of general formula (HP-1),

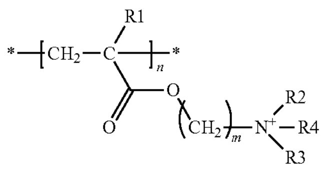

(HP-1)

in which R1=—H or —$CH_3$, R2, R3 and R4 independently of one another are selected from $C_1$-$C_4$ alkyl, alkenyl or hydroxyalkyl groups, m=1, 2, 3 or 4, n is a natural number and X− is a physiologically acceptable organic or inorganic anion, as well as copolymers consisting substantially of the monomer units shown in formula (HP-1) and nonionogenic monomer units, are particularly preferred cationic polymeric gel formers. In the context of these polymers, preferred according to the invention are those for which at least one of the following conditions applies:

R1 represents a methyl group

R2, R3 and R4 are methyl groups, m has the value 2,

As a physiologically acceptable counter ion X—, for example, halide ions, sulfate ions, phosphate ions, methosulfate ions as well as organic ions such as lactate-, citrate-, tartrate- and acetate ions are considered. Halide ions are preferred, in particular chloride.

One particularly suitable homopolymer is the One particularly poly(methacryloxyethyltrimethylammonium) chloride (crosslinked, if desired) having the INCI name Polyquaternium-37. The crosslinking can be carried out, if desired, with the help of olefinically poly-unsaturated compounds, for example, divinylbenzene, tetraallyloxyethane, methylene bisacrylamide, diallyl ether, polyallyl polyglyceryl ether, or allyl ethers of sugars or sugar derivatives, such as erythritol, pentaerythritol, arabitol, mannitol, sorbitol, sucrose or glucose. Methylene bisacrylamide is a preferred crosslinking agent.

The homopolymer is preferably used in the form of a non-aqueous polymer dispersion, which should not have a polymer content of less than 30 wt.-%. Such polymer dispersions are available under the names Salcare®SC 95 (approx. 50% polymer content, further component: mineral oil (INCI name: mineral oil) and tridecyl-polyoxy-propylene -polyoxyethylene ether (INCI name: PPG-1-trideceth-6) and Salcare® SC 96 (approx. 50% polymer content, further components: mixture of diesters of propylene glycol with a mixture of caprylic and capric acid (INCI name: propylene glycol dicaprylate/dicaprate) and tridecyl-polyoxy-propylene-polyoxyethylene ether (INCI name: PPG-1-trideceth-6).

Copolymers comprising monomer units according to formula (HP-1) contain as nonionogenic monomer units preferably acrylamide, methacrylamide, acrylic acid $C_1$-$C_4$ alkyl ester and methacrylic acid $C_1$-$C_4$ alkyl ester. Among these, non-ionic monomers, acrylamide is particularly preferred. These copolymers can also be cross-linked like the homopolymers described above. A preferred copolymer according to the invention is a crosslinked acrylamide methacroyl oxyethyl trimethyl ammonium chloride copolymer. Such copolymers, in which the monomers are present in a weight ratio of about 20:80, are commercially available as approx. 50% non-aqueous polymer dispersion under the name Salcare® SC 92.

In another preferred embodiment, naturally occurring thickening agents are used. Preferred thickening agents of this embodiment are, for example, nonionic guar gums. According to the invention, both modified and unmodified guar gums can be used. Unmodified guar gums are marketed, for example, under the trade name Jaguar® C from Rhone Poulenc. Modified guar gums which are preferred according to the invention contain $C_1$-$C_6$ hydroxyalkyl groups. The groups are preferably hydroxymethyl, hydroxyethyl, hydroxypropyl and hydroxybutyl. Such modified guar gums are well known in the art and can be prepared, for example, by reacting the guar gums with alkylene oxides. The degree of hydroxyalkylation, which corresponds to the number of used alkylene oxide molecules in proportion to the number of the free hydroxyl groups of guar gum, is preferably between 0.4 to 1.2. Such modified guar gums are commercially available under the trade names Jaguar® HP8, Jaguar® HP60, Jaguar® HP120, Jaguar® DC 293 and Jaguar® HP105 from Rhone Poulenc.

Further suitable natural thickening agents are also already known from the prior art.

According to this embodiment, biosaccharide gums of microbial origin, such as scleroglucan gums or xanthan gums, gums from plant exudates, such as gum arabic, ghatti gum, karaya gum, tragacanth gum, carrageenan gum, agar-agar, locust bean gum, pectins, alginates, starch fractions and derivatives, such as amylose, amylopectin and dextrins, cellulose derivatives such as methylcellulose, carboxyalkylcelluloses and hydroxyalkylcelluloses, are still preferred.

Preferred hydroxyalkylcelluloses are, in particular, the hydroxyethylcelluloses, which are marketed under the names Cellosize® from Amerchol and Natrosol® from Hercules. Suitable carboxyalkyl celluloses are in particular the carboxymethylcelluloses as marketed under the names Blanose® from Aqualon, Aquasorb® and Ambergum® from Hercules and Cellgon® from Montello.

Preference is also given to starch and derivatives thereof. Starch is a storage material of plants, which occurs mainly in tubers and roots, in grain seeds, and in fruits, and can be obtained from a variety of plants in high yield. The polysaccharide, which is insoluble in cold water and forms a colloidal solution in boiling water, for example, can be obtained from potatoes, manioc, sweet potatoes, maranta, corn, grains, rice, legumes such as peas and beans, bananas or the marrow of certain types of palm (for example, the sago palm). According to the invention, natural, plant-derived starches and/or chemically or physically modified starches can be used. Modification can be achieved, for example, by introducing different functional groups on one or more of the hydroxyl groups of the starch. These are usually esters, ethers or amides of starch having optionally substituted C1-C40 radicals. Particularly advantageous is an etherified corn starch with 2-hydroxypropyl group, as is marketed, for example, by National Starch under the trade name Amaze®.

However, nonionic, fully synthetic polymers, such as for example polyvinyl alcohol or polyvinylpyrrolidone, can also be used as thickening agents according to the invention. Preferred nonionic, fully synthetic polymers are marketed for example by BASF under the trade name Luviskol®. Such nonionic polymers also allow, in addition to their excellent thickening properties, a significant improvement in the sensory feeling of the resulting preparations.

As inorganic thickening agents, phyllosilicates (polymeric, crystalline sodium disilicates) have proven to be particularly suitable in the context of the present invention. In particular tone, in particular, magnesium aluminum silicates, such as bentonite, particularly smectites, such as montmorillonite or hectorite, which may also be optionally suitably modified, and synthetic phyllosilicates, such as the magnesium phyllosilicates marketed by the company Süd Chemie under the trade name Optigel®, are preferred.

To further increase the performance of the oxidative dyes, at least one optionally hydrated $SiO_2$ compound is additionally preferably added. It may be preferred according to the invention to use the optionally hydrated $SiO_2$ compounds in amounts of 0.05 wt. % to 15 wt. %, particularly preferably in amounts of 0.15 wt. % to 10 wt. % and very particularly preferably in amounts of 0.2 wt. % to 5 wt. %, in each case based on the composition. The specified amounts in each case reflect here the content of the $SiO_2$ compounds (without the water content thereof) in the agents.

With regard to the optionally hydrated $SiO_2$ compounds, the present invention is in principle subject to no limitations. Preference is given to silicic acids, oligomers thereof and polymers thereof, and also salts thereof. Preferred salts are the alkali metal salts, in particular the potassium and sodium salts. The sodium salts are very particularly preferred.

The optionally hydrated $SiO_2$ compounds may be present in different forms. According to the invention, preference is given to using the $SiO_2$ compounds in the form of silica gels, or particularly preferably as water glass. These $SiO_2$ compounds may sometimes be present in aqueous solution.

Very particularly preferred according to the invention are water glasses, which are formed from a silicate of formula $(SiO_2)_n(Na_2O)_m(K_2O)_P$, where n represents a positive rational number, and m and p, independently of one another, represent a positive rational number or 0, with the proviso that at least one of the parameters m or p be different from 0, and the ratio between n and the sum of m and p be between 1,4 and 4:1, are likewise preferred. Preference is given to metasilicates in which the ratio between n and the sum of m and p is 1.2 or below.

Besides the components described by the empirical formula, the water glasses may also contain further additives in small amounts, such as for example phosphates or magnesium salts.

Water glasses which are particularly preferred according to the invention are marketed inter alia by Henkel under the names Ferrosil® 119, Natronwasserglas 40/42, Portil® A, Portil® AW and Portil® W and by Akzo under the name Britesil® C20.

The oxidation dyes are preferably packaged as flowable preparations.

The agents according to the invention may also contain further active substances, auxiliaries and additives, such as for example

- nonionic polymers, such as for example vinylpyrrolidinone/vinyl acrylate copolymers, polyvinylpyrrolidinone, vinylpyrrolidinone/vinyl acetate copolymers, polyethylene glycols and polysiloxanes;
- silicones, such as volatile or non-volatile, straight-chain, branched or cyclic, crosslinked or non-crosslinked polyalkylsiloxanes (such as dimethicones or cyclomethicones), polyarylsiloxanes and/or polyalkylarylsiloxanes, in particular polysiloxanes having organofunctional groups, such as substituted or unsubstituted amines (amodimethicones), carboxyl, alkoxy and/or hydroxyl groups (dimethicone copolyols), linear polysiloxane(A)/polyoxyalkylene(B) block copolymers, grafted silicone polymers having a non-silicone-containing organic backbone or having a polysiloxane backbone, such as for example the commercial product Abil B 8832 from Degussa, which is marketed under the INCI name Bis-PEG/PPG-20/20 Dimethicone, or mixtures thereof;
- cationic polymers such as quaternized cellulose ethers, polysiloxanes having quaternary groups, dimethyldiallyl ammonium chloride polymers, acrylamide dimethyldiallyl ammonium chloride copolymers, dimethylaminoethyl methacrylate-vinylpyrrolidinone copolymers quaternized with diethyl sulfate, vinylpyrrolidinone-imidazolinium methochloride copolymers, and quaternized polyvinyl alcohol;
- zwitterionic and amphoteric polymers, such as for example acrylamidopropyl-trimethylammonium chloride/acrylate copolymers and octylacrylamide/methyl methacrylate/tert-butylaminoethyl methacrylate/2-hydroxypropyl methacrylate copolymers, diallyldimethylammonium chloride/acrylate copolymers, t-butylaminoethyl methacrylate/N-(1,1,3,3-tetramethylbutyl) acrylamide/acrylate(/methacrylate) copolymers;
- anionic polymers, such as for example polyacrylic acids, crosslinked polyacrylic acids, vinyl acetate/crotonic acid copolymers, vinylpyrrolidinone/vinyl acrylate copolymers, vinyl acetate/butyl maleate/isobornyl acrylate copolymers, methyl vinyl ether/maleic anhydride copolymers and acrylic acid/ethyl acrylate/N-t -butylacrylamide terpolymers,
- further thickening agents, such as agar-agar, guar gum, alginates, xanthan gum, gum arabic, karaya gum, locust bean flour, linseed gum, dextrans, cellulose derivatives, for example methyl cellulose, hydroxyalkyl cellulose and carboxymethyl cellulose, starch fractions and derivatives, such as amylose, amylopectin and dextrins, clays, such as for example bentonite or fully synthetic hydrocolloids, such as for example polyvinyl alcohol,
- structurants, such as glucose, maleic acid and lactic acid,
- hair-conditioning compounds, such as phospholipids, for example soya lecithin, egg lecithin and cephalins as well as silicone oils,
- perfume oils, dimethyl isosorbide and cyclodextrins,
- solvents and solubilizers, such as ethanol, isopropanol, ethylene glycol, propylene glycol, glycerol, and diethylene glycol,
- fiber-structure-improving active ingredients, in particular mono-, di-, and oligosaccharides, such as, for example, glucose, galactose, fructose, fruit sugar, and lactose.
- quaternized amines, such as methyl-1-alkylamidoethyl-2-alkylimidazolinium methosulfate
- defoaming agents, such as silicones,
- dyes for coloring the agent,
- anti-dandruff active substances such as piroctone olamine, zinc omadine and climbazole,
- amino acids and oligopeptides, in particular arginine and/or serine,
- protein hydrolysates of animal and/or plant origin, such as for example elastin, collagen, keratin, silk and lactoprotein protein hydrolysates, or almond, rice, pea, potato and wheat protein hydrolysates, as well as those in the form of their fatty acid condensation products or optionally anionically or cationically modified derivatives thereof;
- vegetable oils, for example macadamia nut oil, kukui nut oil, palm oil, amaranth seed oil, peach kernel oil, avocado oil, olive oil, coconut oil, rapeseed oil, sesame oil, jojoba oil, soybean oil, peanut oil, evening primrose oil and tea tree oil
- light stabilizers, in particular derivatized benzophenones, cinnamic acid derivatives and triazines,
- substances for adjusting the pH, such as for example conventional acids, in particular edible acids and bases;
- active substances such as panthenol, pantothenic acid, pantolactone, allantoin, pyrrolidone carboxylic acids and salts thereof, and bisabololl,
- polyphenols, in particular hydroxycinnamic acids, 6,7-dihydroxycoumarin, hydroxybenzoic acids, catechins, tannins, leucoanthocyanidins, anthocyanidins, flavanones, flavones, and flavonols;
- ceramides, preferably the sphingolipids such as ceramide I, ceramide II, ceramide 1, ceramide 2, ceramide 3, ceramide 5 and ceramide 6, or pseudoceramides, such as in particular N-($C_8$-$C_{22}$-acyl)-($C_8$-$C_{22}$-acyl)-hydroxyproline,
- vitamins, provitamins and vitamin precursors, in particular those of groups A, $B_3$, $B_5$,$B_6$, C, E, F and H,
- plant extracts, such as for example the extracts of aloe vera, angelica, anise, apricot, benzoin, bergamot, birch, nettle, calamus, blackcurrant, costus, hibiscus, oak bark, elemi, tarragon, pine needles, galbanum, geranium, ginseng, grapefruit, guaiac wood, green tea, hamamelis, restharrow, hops, coltsfoot, ginger root, iris, jasmine, chamomile, cardamom, clover, burdock root, pine, kiwi fruit, coconut, coriander, caraway, mountain pine, lavender, lemon grass, lily, lime, linden blossom, lychee, mace, malva, almond, mango, lemon balm, melon, meristem, myrrh, neroli, olibanum, opoponax, orange, patchouli, petitgrain, stone pine, wild thyme, rooibos, rose, rosemary, horse chestnut, sandalwood, sage, horsetail, yarrow, celery, spruce, thyme, juniper, vine leaves, hawthorn, wheat, lady's-smock, ylang-ylang, cedar and lemon.
- cholesterol,
- consistency regulators, such as sugar esters, polyol esters or polyol alkyl ethers,
- fats and waxes, such as spermaceti, beeswax, montan wax and paraffins,
- fatty acid alkanolamides,
- swelling and penetration agents, such as glycerol, propylene glycol monoethyl ether, carbonates, hydrogen carbonates, guanidines, ureas, and primary, secondary, and tertiary phosphates,
- turbidity agents, such as latex, styrene/PVP and styrene/acrylamide copolymers;
- pearlescent agents, such as ethylene glycol mono- and distearate and PEG-3 distearate,
- pigments, stabilizing agents for hydrogen peroxide and other oxidizing agents, propellants such as propane-butane mixtures, $N_2O$, dimethyl ether, $CO_2$ and air, antioxidants.

The selection of these additional substances is made by the person skilled in the art according to the desired properties of the agents.

With respect to other optional components and the employed amounts of said components, reference is made expressly to relevant manuals known to the person skilled in the art, e.g., Kh. Schrader, Grundlagen und Rezepturen der Kosmetika, 2nd Edition, Hüthig Buch Verlag, Heidelberg, 1989.

The additional active ingredients and auxiliaries are used in the agents according to the invention preferably in quantities of from, in each case, 0.0001 to 10 wt.-%, in particular of from 0.0005 to 5 wt.-%, relative to the total weight of the application mixture.

Multi-Component Packaging Unit (Kit-of-Parts)

The means according to the invention are means for oxidatively dyeing or dyeing and lightening hair. In the ready-to-use means, the oxidation dye precursors react with the oxidizing agent to form the actual dyes. The means according to the invention are therefore usually packaged as multi-component means, usually as two-component means. The first component (A) here contains the oxidation dye precursors (a) and (b), which is mixed shortly before application with a second component containing the oxidizing agent (c). Usually, both components are mixed with one another in the range of from 1:3 to 3:1, preferably from 1:2 to 2:1. This mixture of the component containing color cream and optionally alkalizing agent (preparation A) and the component containing oxidizing agent (preparation B) is referred to as the application mixture or the ready-to-use means.

A second subject of the present invention is a multi-component packaging unit (kit-of-parts) for oxidatively coloring keratin fibers, in particular human hair, comprising, packaged separately from one another, a first container having a dye (F), which contains (a) at least one oxidation dye precursor of the developer type, selected from the group including p-toluenediamine, 2-methoxymethyl-p-phenylenediamine, 2-(2-hydroxyethyl) -p-phenylenediamine, N,N-bis(2-hydroxy-hydroxyethyl)-p-phenylenediamine, p-phenylenediamine and the physiologically acceptable salts thereof;

(b) isatin and a second container having an oxidation composition (Ox), which contains (c) at least one oxidizing agent from the group consisting of hydrogen peroxide and its addition products with organic or inorganic compounds, wherein the constituents (a), (b) and (c) have already been disclosed in detail in the description of the first subject matter of the invention.

Alternatively, the dye (F) can also be referred to as color cream.

Use of the Combination of (a) and (b) for Producing Natural Tones on the Keratin Fibers A third subject matter of the present invention relates to the use of a combination of (a) at least one oxidation dye precursor of the developer type, selected from the group including p-toluenediamine, 2-methoxymethyl-p-phenylenediamine, 2-(2-hydroxyethyl)-p-phenylenediamine, N,N-bis(2-hydroxy-hydroxyethyl)-p -phenylenediamine, p-phenylenediamine and the physiologically acceptable salts thereof;

(b) isatin in an oxidative dye in order to produce, in the presence of (c) at least one oxidizing agent from the group consisting of hydrogen peroxide and its addition products with organic or inorganic compounds color shades in the natural tone range on keratin fibers, in particular human hair.

Colorations in the natural tone range are understood to mean, for example, the shades of light brown, medium-blond, dark brown, light brown-red, light brown-gold and dark-blond copper.

Method for Oxidatively Dyeing Keratin Fibers

The oxidative dye according to the invention of the first subject matter of the invention or the multicomponent packaging unit, the separately packaged components of which are used for producing said ready-to-use dye, are outstandingly suitable for use in corresponding dyeing methods, A further subject matter of the present invention is therefore a method for oxidatively dyeing keratin fibers, in particular human hair, in which a means, as disclosed in detail in the description of the first subject matter of the invention, is applied to the keratin fibers and rinsed out again after an exposure time.

While the fibers are being exposed to the agent, it can be advantageous to support the dyeing process by applying heat. Heat can be applied by an external heat source, such as e.g. hot air from a hot-air blower, and also, in particular in the case of dyeing the hair of a living subject, by the body temperature of the subject. In the latter possibility, conventionally the part to be dyed is covered with a cap. In particular, the temperature during the exposure time is between 10° C. and 45° C., in particular between 20° C. and 40° C. The dyes according to the invention already give intense colorations at physiologically acceptable temperatures of less than 45° C. Therefore, they are suitable particularly for coloring human hair.

What has been stated regarding the means according to the invention applies, mutatis mutandis, to additional preferred embodiments of the multicomponent packaging unit, use and method according to the invention.

EXAMPLES

1. Production of the Formulations

The following formulas were produced: Unless otherwise noted, the quantitative data are given in weight percent in each case.

TABLE 1

| Basic formula—color cream | F (wt. %) |
|---|---|
| Sodium cetearyl sulfate | 1.3 |
| 2-Octyldodecanol | 2.0 |
| Cetearyl alcohol | 14.9 |

TABLE 1-continued

| Basic formula—color cream | F (wt. %) |
|---|---|
| Glyceryl stearate | 5.4 |
| Glycerol | 2.0 |
| Cocoamidopropyl betaine (40% aqueous solution) | 1.8 |
| Mixture of oxidation dye precursors (mixture OFV) | according to Tables 3 and 4 |
| Ammonia (25% aqueous solution) | 6.0 |
| Sodium sulfite | 0.2 |
| Water (distilled) | up to 100 |

TABLE 2

| Oxidizing agent preparation | OX (wt. %) |
|---|---|
| 1,2-propanediol | 0.5 |
| Paraffinum Liquidum | 0.5 |
| Cetearyl alcohol | 4.0 |
| Ceteareth-20 | 1.2 |
| Hydrogen peroxide (50% aqueous solution) | 12.00 |
| Water (distilled) | up to 100 |

2. Application and Colorimetric Results

The base formulation for the color cream described in Table 1 was prepared. The mixtures of oxidation dye precursors described in Tables 3 and 4 were each incorporated into the color cream. Each of the color creams prepared in this way was mixed in a quantitative ratio of 1:1 with the oxidizing agent preparation OX. Each of the ready-to-use dyes prepared in this way was then applied to a hair strand (Kerling, natural white) and left there for a period of 30 minutes. The application mixture was then rinsed out with a shampoo and dried. The hair strands were then measured colorimetrically (measurement of lab values).

TABLE 3

(all figures in wt. %, based on the total weight of the color cream)

| Mixture OFV | F1 | F2 without RES | F3 | F4 without RES | F5 | F6 without RES |
|---|---|---|---|---|---|---|
| p-toluenediamine (sulfate) | 0.85 | 0.55 | 0.41 | 1.16 | 1.86 | 4.66 |
| Resorcinol | 0.23 | — | 0.10 | — | 0.65 | — |
| 4-chlororesorcinol | 0.13 | — | — | — | — | — |
| 2-methylresorcinol | — | — | 0.04 | — | — | — |
| M-aminophenol | 0.10 | — | 0.02 | — | 0.27 | 0.465 |
| 1-methoxy-2-amino-4-(2-hydroxy-ethylamino)benzene | — | 0.21 | — | 0.004 | — | — |
| 6-hydroxyindole | — | 0.18 | — | — | — | — |
| 2.7-napthalenediol | — | — | 0.01 | — | — | — |
| 2-chloro-6-methyl-3-aminophenol | — | — | — | — | — | 0.014 |
| Isatin | — | 0.06 | — | 0.77 | — | 2.476 |

without RES = without use of resorcinol derivatives

| Coloration with ready-to-use dye F + OX | F1 | F2 without RES | F3 | F4 without RES | F5 | F6 without RES |
|---|---|---|---|---|---|---|
| L | 23.72 | 23.88 | 43.59 | 43.64 | 14.46 | 14.58 |
| a | 5.84 | 7.32 | 4.50 | 5.57 | 3.79 | 3.80 |
| b | 6.49 | 6.48 | 11.46 | 11.46 | 1.74 | 1.70 |
| Shade | light brown | light brown | medium blond | medium blond | dark brown | dark brown |

TABLE 3 continued (all figures in wt. %, based on the total weight of the color cream)

| Mixture OFV | F7 | F8 without RES | F9 | F10 without RES | F11 | F12 without RES |
|---|---|---|---|---|---|---|
| p-toluenediamine (sulfate) | 1.20 | 1.04 | 0.589 | 0.536 | 0.130 | 0.130 |
| 4-amino-3-methylphenol | 0.30 | 0.30 | — | — | 0.380 | 0.54 |
| Resorcinol | 0.07 | — | 0.173 | — | 0.045 | — |
| 4-chlororesorcinol | — | — | 0.045 | — | — | — |
| 2-methylresorcinol | 0.20 | — | 0.046 | — | — | — |
| m-aminophenol | 0.13 | 0.155 | 0.20 | — | — | — |
| 5-amino 2-methylphenol | 0.32 | 0.32 | — | 0.142 | 0.18 | 0.235 |
| 1-naphthol | — | — | — | — | 0.05 | — |
| 2-amino-3-hydroxypyridine | 0.20 | 0.24 | 0.025 | — | 0.16 | 0.1330 |
| 4-amino-3-nitrophenol | 0.33 | 0.39 | — | — | — | — |
| 2-amino-6-chloro-4-nitrophenol | — | — | 0.02 | 0.07 | 0.36 | 0.33 |
| isatin | — | 0.14 | — | 0.189 | — | 0.225 |

| Coloration with ready-to-use dye F + OX | F7 | F8 without RES | F9 | F10 without RES | F11 | S12 without RES |
|---|---|---|---|---|---|---|
| L | 15.05 | 15.09 | 25.08 | 25.06 | 31.03 | 31.01 |
| a | 11.00 | 11.00 | 7.65 | 11.03 | 24.80 | 11.00 |
| b | 3.59 | 3.56 | 3.27 | 3.91 | 27.30 | 27.31 |
| Shade | natural light brown-red | natural light brown-red | light brown-gold | light brown-gold | dark blond copper | dark blond copper |

The ready-to-use dyes that have been obtained using the color creams F2, F4 and F6 dyed the hair in very intense, natural shades in the range of dark brown, medium brown, and dark blond. The shade effect of these colorations showed an almost exact color match with the resorcinol-containing dyes known from the prior art based on the color creams F1, F3, and F5.

Shades in the natural tone range with a reddish color effect could also be obtained by using dyes according to the invention using the color creams F8, F10 and F12. The shades in the red-blond and copper-blond range corresponded very well in terms of color to the resorcinol-containing dyes known from the prior art based on the color creams F7, F9, and F11.

3. Other Colorations

For further colorations, the base formulation described in Table 1 was prepared for the color cream. The mixtures of oxidation dye precursors described in Table 4 were each incorporated into the color cream. Each of the color creams prepared in this way was mixed in a quantitative ratio of 1:1 with the oxidizing agent preparation OX. Each of the ready-to-use dyes thus produced was then applied to a hair strand (Kerling, natural white) and left there for a period of 30 minutes. The application mixture was then rinsed out with a shampoo and dried. Thereafter, the hair strands were colorimetrically measured (measurement of lab values).

TABLE 4

(all figures in wt. %, based on the total weight of the color cream)

| Mixture OFV | F13 | F14 | F15 | F16 | F17 | F18 |
|---|---|---|---|---|---|---|
| P-toluenediamine sulfate | 0.016 | — | — | — | — | — |
| N,N-bis(2-hydroxyethyl)-p-phenylenediamine sulfate | — | 0.55 | 0.94 | — | — | — |
| 4-amino-3-methylphenol | — | — | — | 0.3000 | — | 0.53 |
| 2-methoxymethyl-p-phenylenediamine diamine | 1.39 | 0.495 | 1.8000 | 1.3480 | 0.79 | 0.19 |
| M-aminophenol | 0.103 | — | 0.4540 | 0.3000 | — | — |
| 5-amino 2-methylphenol | — | — | — | 0.3200 | 0.38 | 0.297 |
| 6-hydroxyindole | 0.139 | — | — | — | — | — |
| Isatin | 1.067 | 0.75 | 1.60 | 0.10 | 0.306 | 0.228 |
| 2-amino-3-hydroxypyridine | — | — | — | 0.62 | — | 0.138 |
| 2-amino-6-chloro-4-nitrophenol | — | — | — | — | 0.0500 | 0.30 |
| Coloration with ready-to-use dye F + OX | F13 | F14 | F15 | F16 | F17 | F18 |
| L | 23.76 | 42.74 | 18.40 | 15.17 | 25.18 | 4.50 |
| a | 5.84 | 2.70 | 3.79 | 11.01 | 11.00 | 11.00 |
| b | 6.51 | 8.52 | 1.20 | 3.56 | 3.88 | 27.31 |
| Shade | light brown | medium blond | dark brown | natural light brown-red | brown gold | dark blond copper |

TABLE 4 continued (all figures in wt. %, based on the total weight of the color cream)

| Mixture OFV | F19 | F20 | F21 | F22 | F23 | F24 |
|---|---|---|---|---|---|---|
| P-toluenediamine sulfate | — | — | 1.9200 | — | — | — |
| 4-amino-3-methylphenol | — | — | — | — | — | 0.30 |
| 2-(2-hydroxy-ethyl)-p-phenylenediamine | — | 2.2900 | — | 1.985 | 0.77 | 1.50 |
| 1-hydroxyethyl 4,5-diamino pyrazole sulfate | 0.0004 | 0.0004 | 0.005 | — | — | — |
| 2-methoxymethyl-p-phenylenediamine diamine | 2.30 | — | — | — | — | — |
| m-aminophenol | 0.187 | 0.08 | 0.079 | — | — | 0.068 |
| 5-amino 2-methylphenol | 0.25 | 0.1080 | 0.029 | — | 0.22 | 0.32 |
| 1-methoxy-2-amino-4-(2-hydroxyethyl-amino)-benzene | — | — | — | 0.1550 | — | — |
| 6-hydroxyindole | — | — | — | 0.2830 | — | — |
| Isatin | 0.675 | 0.59 | 0.625 | 0.7740 | 0.1900 | 0.10 |
| 2-amino-3-hydroxypyridine | 0.54 | 0.391 | 0.389 | — | — | 0.54 |
| 4-amino-3-nitrophenol | — | 0.0033 | 0.003 | — | 0.06 | — |
| Coloration with ready-to-use dye F + OX | F19 | F20 | F21 | F22 | F23 | F24 |
| L | 15.06 | 15.08 | 15.04 | 23.80 | 25.06 | 15.41 |
| a | 11.00 | 11.00 | 11.00 | 5.97 | 11.00 | 10.99 |
| b | 3.59 | 3.60 | 3.60 | 6.47 | 3.80 | 3.56 |
| Shade | natural light brown-red | natural light brown-red | natural light brown-red | light brown | light brown gold | natural light brown-red |

What is claimed is:

1. A multi-component packaging unit for oxidatively dyeing keratin fibers, the multi-component packaging unit comprising:
- a first container containing a dye, the dye comprising:
  - at least one oxidation dye precursor of the developer type selected from the group consisting of p-toluylenediamine, 2-methoxymethyl-p-phenylenediamine, 2-(2-hydroxy-hydroxyethyl)-p-phenylenediamine, N,N-bis(2-hydroxy-hydroxyethyl)-p-phenylenediamine, p-phenylenediamine and physiologically acceptable salts thereof;
  - isatin; and
  - at least one oxidation dye precursor of the coupler type selected from the group consisting of 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis (2,4-diaminophenyl)propane, 2,6-bis(2'-hydroxyethyl)-1-methylbenzene, 1-amino-3-bis (2-hydroxyethyl) aminobenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, any mixture thereof, and any physiologically acceptable salt thereof; and
- a second container containing an oxidation composition, the oxidation composition comprising:
  - at least one oxidizing agent selected from the group consisting of hydrogen peroxide and its addition products with organic or inorganic compounds,
- wherein the first contained and the second container are packaged separately from one another.

2. The multi-component packaging unit of claim 1, wherein the at least one oxidation dye precursor of the developer type is selected from the group consisting of p-toluylenediamine, 2-methoxymethyl-p-phenylenediamine, and physiologically acceptable salts thereof.

3. The multi-component packaging unit of claim 1, wherein the at least one oxidation dye precursor of the developer type is present in an amount, based on the total weight of the dye and oxidation composition, ranging from 0.001 to 10.0 wt. %.

4. The multi-component packaging unit of claim 3, wherein the at least one oxidation dye precursor of the developer type is present in an amount, based on the total weight of the dye and oxidation composition, ranging from 0.01 to 6.0 wt %.

5. The multi-component packaging unit of claim 4, wherein the at least one oxidation dye precursor of the developer type is present in an amount, based on the total weight of the dye and oxidation composition, ranging from 0.1 to 5.0 wt. %.

6. The multi-component packaging unit of claim 1, wherein the isatin is present in an amount, based on the total weight of the dye and oxidation composition, ranging from 0.001 to 10 wt. %.

7. The multi-component packaging unit of claim 6, wherein the isatin is present in an amount, based on the total weight of the dye and oxidation composition, ranging from 0.01 to 5 wt. %.

8. The multi-component packaging unit of claim 7, wherein the isatin is present in an amount, based on the total weight of the dye and oxidation composition, ranging from 0.15 to 2.5 wt. %.

9. The multi-component packaging unit of claim 1, wherein a weight ratio of the at least one oxidation dye precursor of the developer type to the isatin in the dye has a value ranging from 2:1 to 1:2.

10. The multi-component packaging unit of claim 9, wherein a weight ratio of the at least one oxidation dye precursor of the developer type to the isatin in the dye has a value ranging from 1.7:1 to 1.2:1.

11. The multi-component packaging unit of claim 1, wherein the at least one oxidizing agent is present in an amount, based on the total weight of the dye, ranging from 0.5 to 20 wt. %.

12. The multi-component packaging unit of claim 11, wherein the at least one oxidizing agent is present in an amount, based on the total weight of the dye, ranging from 2.5 to 10 wt. %.

13. The multi-component packaging unit of claim 1, wherein the at least one oxidation dye precursor of the coupler type is selected from the group consisting of 3-aminophenol, 5-amino-2-methylphenol, 3-amino-2-chloro-6-methylphenol, 2-amino-3-hydroxypyridine, 1-methoxy-2-amino-4-(2-hydroxyethylamino)enzene, 6-hydroxyindole, any mixture thereof, and any physiologically acceptable salt thereof.

14. The multi-component packaging unit of claim 1, wherein the at least one oxidation dye precursor of the coupler type is present in an amount, based on the total weight of the dye and oxidation composition, ranging from 0.001 to 10 wt. %.

15. The multi-component packaging unit of claim 1, wherein in the dye further comprises at least one resorcinol-type coupler present in an amount, based on the total weight of the dye and oxidation composition, below 0.1 wt. %.

16. The multi-component packaging unit of claim 1, wherein the dye further comprises at least one surfactant selected from the group of anionic surfactants, amphoteric surfactants, zwitterionic surfactants, and nonionic surfactants.

17. The agent multi-component packaging unit of claim 1, wherein the agent comprises less than 25 wt % of fatty components, based on the total weight of the dye and oxidation composition.

* * * * *